United States Patent [19]
Knappe et al.

[11] Patent Number: 5,989,867
[45] Date of Patent: Nov. 23, 1999

[54] DNA ENCODING IL-10-LIKE HOMOLOGUE; RELATED REAGENTS

[76] Inventors: Andrea Knappe, Karlsbader Strasse 5, Erlangen, Germany, D-91058; Helmut Fickenscher, Im Heuschlag 20, Erlangen, Germany, D-91054; Bernhard Fleckenstein, Schlaifhausen 228, Wiesenthau, Germany, D-91368

[21] Appl. No.: 08/934,959

[22] Filed: Sep. 22, 1997

Related U.S. Application Data

[60] Provisional application No. 60/027,368, Sep. 23, 1996.
[51] Int. Cl.$^6$ .................................................. C12N 15/24
[52] U.S. Cl. .................. 435/69.52; 435/69.5; 435/252.3; 435/320.1; 536/23.5; 536/24.3
[58] Field of Search .................................. 536/23.5, 24.3; 438/69.5, 69.52, 252.3, 320.1

[56] References Cited

U.S. PATENT DOCUMENTS 5,231,012  7/1993  Mosmann et al. ................... 435/69.52

OTHER PUBLICATIONS

Helene M. Martin, et al., *Gene* 159(2):187–191, 1995. "Cloning and characterisation of an ovine interleukin–10–encoding cDNA".

Anthony R. Mire–Sluis, et al., *Journal of Immunological Methods*, 187(2):191–199, 1995. "Quantitative cell line based bioassays for human cytokines".

Jan E. de Vries and Rene de Waal Malefyt, *Interleukin 10*, R.G. Landes Company: Austin, Texas, 1995.

G.S. Hudson, et al., *GenBank*, Accession No. M11924, pp. 1–5, Sep. 1, 1988. "The short unique region of the B95–8 Epstein–Barr virus genome".

Kevin W. Moore, et al., *GenBank*, Accession No. M37897, pp. 1–2, Jun. 12, 1991. "Homology of cytokine sythesis inhibitory factor (IL–10) to the Epstein–Barr virus gene BCRFI".

H.–J. Rode, et al., *GenBank*, Accession No. L08504, p. 1, Aug. 2, 1993. "The genome of equine herpesvirus type 2 harbors an interleukin 10 (IL10)–like gene".

P. Vieira, et al., *GenBank*, Accession No. M57627, pp. 1–2, Mar. 7, 1995. "Isolation and expression of human cytokine synthesis inhibitory factor cDNA clones: homology to Epstein–Barr virus open reading frame BCRFI".

Adams et al Accession # B69652.

Adams et al Accession # B48149.

*Primary Examiner*—Garnette D. Draper
*Attorney, Agent, or Firm*—Gerald P. Keleher; Edwin P. Ching

[57] ABSTRACT

Purified genes encoding cytokine from a mammal, reagents related thereto including purified proteins, specific antibodies, and nucleic acids encoding this molecule are provided. Methods of using said reagents and diagnostic kits are also provided.

29 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 1076 base pairs
      (B) TYPE: nucleic acid
      (C) STRANDEDNESS: single
      (D) TOPOLOGY: linear (ii) MOLECULE TYPE: cDNA (ix) FEATURE:
    (A) NAME/KEY: CDS
    (B) LOCATION: 36..548

(ix) FEATURE:
    (A) NAME/KEY: mat_peptide
    (B) LOCATION: 99..548

(xi) SEQUENCE DESCRIPTION: SEQ ID NO:1:

```
CTGTGAGTGA CACACGCTGA GTGGGGTGAA GGGAA ATG CTG GTG AAT TTC ATT           53
                                      Met Leu Val Asn Phe Ile
                                      -21 -20

TTG AGG TGT GGG TTG CTG TTA GTC ACT CTG TCT CTT GCC ATT GCA AAG         101
Leu Arg Cys Gly Leu Leu Leu Val Thr Leu Ser Leu Ala Ile Ala Lys
-15             -10              -5                           1

CAC AAG CAA TCT TCC TTC ACC AAA AGT TGT TAC CCA AGG GGA ACA TTG         149
His Lys Gln Ser Ser Phe Thr Lys Ser Cys Tyr Pro Arg Gly Thr Leu
             5                  10                  15

TCC CAA GCT GTT GAC GCT CTC TAT ATC AAA GCA GCA TGG CTC AAA GCA         197
Ser Gln Ala Val Asp Ala Leu Tyr Ile Lys Ala Ala Trp Leu Lys Ala
         20                  25                  30

ACG ATT CCA GAA GAC CGC ATA AAA AAT ATA CGA TTA TTA AAA AAG AAA         245
Thr Ile Pro Glu Asp Arg Ile Lys Asn Ile Arg Leu Leu Lys Lys Lys
     35                  40                  45

ACA AAA AAG CAG TTT ATG AAA AAC TGT CAA TTT CAA GAA CAG CTT CTG         293
Thr Lys Lys Gln Phe Met Lys Asn Cys Gln Phe Gln Glu Gln Leu Leu
 50                  55                  60                  65

TCC TTC TTC ATG GAA GAC GTT TTT GGT CAA CTG CAA TTG CAA GGC TGC         341
Ser Phe Phe Met Glu Asp Val Phe Gly Gln Leu Gln Leu Gln Gly Cys
                 70                  75                  80

AAG AAA ATA CGC TTT GTG GAG GAC TTT CAT AGC CTT AGG CAG AAA TTG         389
Lys Lys Ile Arg Phe Val Glu Asp Phe His Ser Leu Arg Gln Lys Leu
             85                  90                  95

AGC CAC TGT ATT TCC TGT GCT TCA TCA GCT AGA GAG ATG AAA TCC ATT         437
Ser His Cys Ile Ser Cys Ala Ser Ser Ala Arg Glu Met Lys Ser Ile
         100                 105                 110

ACC AGG ATG AAA AGA ATA TTT TAT AGG ATT GGA AAC AAA GGA ATC TAC         485
Thr Arg Met Lys Arg Ile Phe Tyr Arg Ile Gly Asn Lys Gly Ile Tyr
     115                 120                 125

AAA GCC ATC AGT GAA CTG GAT ATT CTT CTT TCC TGG ATT AAA AAA TTA         533
Lys Ala Ile Ser Glu Leu Asp Ile Leu Leu Ser Trp Ile Lys Lys Leu
130                 135                 140                 145

TTG GAA AGC AGT CAG TAAACCAAAG CCAAGTACAT TGATTTTACA GTTATTTGA          588
Leu Glu Ser Ser Gln
                150

AATACAATAA GAACTGCTAG AAATATGTTT ATAACAGTCT ATTTCTTTTA AAAACTTTTT        648

AACATAATAC TGACGGCATG TTAGGTGATT CAGAATAGAC AAGAAGGATT TAGTAAATTA        708

ACGTTTTGGA TATAAGTTGT CACTAATTTG CACATTTTCT GTGTTTTCAA ATAATGTTTC        768

CATTCTGAAC ATGTTTTGTC ATTCACAAGT ACATTGTGTC AACTTAATTT AAAGTATGTA        828

ACCTGAATTA ACTCGTGTAA TATTTGTGTG TGGAGTGGGA TGTGGGGGGT GGAGGGGGAA        888

TGACAGATTT CTGGAATGCA ATGTAATGTT ACTGAGACTT AAATAGATGT TATGTATATG        948

ATTGTCTGTT TAAGTGTTTG AAAATTGTTA ATTATGCCCA GTGTGAACTT AGTACTTAAC       1008

ACATTTTGAT TTTAATTAAA TAAATTGGGT TTCCTTCTCA AAAAAAAAAA AAAAAAAAA        1068

AAAAAAAA                                                               1076
```

(2) INFORMATION FOR SEQ ID NO:2:

(i) SEQUENCE CHARACTERISTICS:
    (A) LENGTH: 171 amino acids
    (B) TYPE: amino acid
    (D) TOPOLOGY: linear (ii) MOLECULE TYPE: protein (xi) SEQUENCE DESCRIPTION: SEQ ID NO:2:

```
Met Leu Val Asn Phe Ile Leu Arg Cys Gly Leu Leu Val Thr Leu
-21 -20             -15                 -10

Ser Leu Ala Ile Ala Lys His Lys Gln Ser Ser Phe Thr Lys Ser Cys
 -5              1               5                    10

Tyr Pro Arg Gly Thr Leu Ser Gln Ala Val Asp Ala Leu Tyr Ile Lys
             15              20              25

Ala Ala Trp Leu Lys Ala Thr Ile Pro Glu Asp Arg Ile Lys Asn Ile
             30              35              40

Arg Leu Leu Lys Lys Thr Lys Lys Gln Phe Met Lys Asn Cys Gln
     45              50              55

Phe Gln Glu Gln Leu Leu Ser Phe Phe Met Glu Asp Val Phe Gly Gln
 60              65              70              75

Leu Gln Leu Gln Gly Cys Lys Lys Ile Arg Phe Val Glu Asp Phe His
             80              85              90

Ser Leu Arg Gln Lys Leu Ser His Cys Ile Ser Cys Ala Ser Ser Ala
             95             100             105

Arg Glu Met Lys Ser Ile Thr Arg Met Lys Arg Ile Phe Tyr Arg Ile
         110             115             120

Gly Asn Lys Gly Ile Tyr Lys Ala Ile Ser Glu Leu Asp Ile Leu Leu
        125             130             135

Ser Trp Ile Lys Lys Leu Leu Glu Ser Ser Gln
140             145             150
```

(2) INFORMATION FOR SEQ ID NO:3:

(i) SEQUENCE CHARACTERISTICS:
    (A) LENGTH: 179 amino acids
    (B) TYPE: amino acid
    (C) STRANDEDNESS: Not Relevant
    (D) TOPOLOGY: Not Relevant (ii) MOLECULE TYPE: peptide (xi) SEQUENCE DESCRIPTION: SEQ ID NO:3:

```
Met Phe Arg Ala Ser Leu Leu Cys Cys Leu Val Leu Leu Ala Gly Val
 1               5              10              15

Trp Ala Asp Asn Lys Tyr Asp Ser Glu Ser Gly Asp Asp Cys Pro Thr
         20              25              30

Leu Pro Thr Ser Leu Pro His Met Leu His Glu Leu Arg Ala Ala Phe
             35              40              45

Ser Arg Val Lys Thr Phe Phe Gln Met Lys Asp Gln Leu Asp Asn Met
     50              55              60

Leu Leu Asp Gly Ser Leu Leu Glu Asp Phe Lys Gly Tyr Leu Gly Cys
 65              70              75              80

Gln Ala Leu Ser Glu Met Ile Gln Phe Tyr Leu Glu Glu Val Met Pro
             85              90              95

Gln Ala Glu Asn His Ser Thr Asp Gln Glu Lys Asp Lys Val Asn Ser
            100             105             110

Leu Gly Glu Lys Leu Lys Thr Leu Arg Val Arg Leu Arg Arg Cys His
            115             120             125
```

```
Arg Phe Leu Pro Cys Glu Asn Lys Ser Lys Ala Val Glu Gln Val Lys
    130                 135                 140

Ser Ala Phe Ser Lys Leu Gln Glu Lys Gly Val Tyr Lys Ala Met Ser
145                 150                 155                 160

Glu Phe Asp Ile Phe Ile Asn Tyr Ile Glu Ala Tyr Met Thr Thr Lys
                165                 170                 175

Met Lys Asn
```

(2) INFORMATION FOR SEQ ID NO:4:

(i) SEQUENCE CHARACTERISTICS:
        (A) LENGTH: 170 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:4:

```
Met Glu Arg Arg Leu Val Val Thr Leu Gln Cys Leu Val Leu Leu Tyr
1                   5                  10                  15

Leu Ala Pro Glu Cys Gly Gly Thr Asp Gln Cys Asp Asn Phe Pro Gln
                 20                  25                  30

Met Leu Arg Asp Leu Arg Asp Ala Phe Ser Arg Val Lys Thr Phe Phe
             35                  40                  45

Gln Thr Lys Asp Glu Val Asp Asn Leu Leu Lys Glu Ser Leu Leu
 50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                 85                  90                  95

Glu Ala Lys Asp His Val Asn Ser Leu Gly Glu Asn Leu Lys Thr Leu
            100                 105                 110

Arg Leu Arg Leu Arg Arg Cys His Arg Phe Leu Pro Cys Glu Asn Lys
        115                 120                 125

Ser Lys Ala Val Glu Gln Ile Lys Asn Ala Phe Asn Lys Leu Gln Glu
    130                 135                 140

Lys Gly Ile Tyr Lys Ala Met Ser Glu Phe Asp Ile Phe Ile Asn Tyr
145                 150                 155                 160

Ile Glu Ala Tyr Met Thr Ile Lys Ala Arg
                165                 170
```

(2) INFORMATION FOR SEQ ID NO:5:

(i) SEQUENCE CHARACTERISTICS:
        (A) LENGTH: 178 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:5:

```
Met Pro Gly Ser Ala Leu Leu Cys Cys Leu Leu Leu Leu Thr Gly Met
1                   5                  10                  15

Arg Ile Ser Arg Gly Gln Tyr Ser Arg Glu Asp Asn Asn Cys Thr His
                 20                  25                  30

Phe Pro Val Gly Gln Ser His Met Leu Leu Glu Leu Arg Thr Ala Phe
             35                  40                  45

Ser Gln Val Lys Thr Phe Phe Gln Thr Lys Asp Gln Leu Asp Asn Ile
```

```
          50                  55                  60
Leu Leu Thr Asp Ser Leu Met Gln Asp Phe Lys Gly Tyr Leu Gly Cys
 65                  70                  75                  80

Gln Ala Leu Ser Glu Met Ile Gln Phe Tyr Leu Val Glu Val Met Pro
                 85                  90                  95

Gln Ala Glu Lys His Gly Pro Glu Ile Lys Glu His Leu Asn Ser Leu
            100                 105                 110

Gly Glu Lys Leu Lys Thr Leu Arg Met Arg Leu Arg Arg Cys His Arg
        115                 120                 125

Phe Leu Pro Cys Glu Asn Lys Ser Lys Ala Val Glu Gln Val Lys Ser
    130                 135                 140

Asp Phe Asn Lys Leu Gln Asp Gln Gly Val Tyr Lys Ala Met Asn Glu
145                 150                 155                 160

Phe Asp Ile Phe Ile Asn Cys Ile Glu Ala Tyr Met Met Ile Lys Met
                165                 170                 175

Lys Ser
```

NFORMATION FOR SEQ ID NO:6:

(i) SEQUENCE CHARACTERISTICS:
    (A) LENGTH: 178 amino acids
    (B) TYPE: amino acid
    (C) STRANDEDNESS: Not Relevant
    (D) TOPOLOGY: Not Relevant ii) MOLECULE TYPE: peptide (xi) SEQUENCE DESCRIPTION: SEQ ID NO:6:

```
Met His Ser Ser Ala Leu Leu Cys Cys Leu Val Leu Leu Thr Gly Val
 1               5                  10                  15

Arg Ala Ser Pro Gly Gln Gly Thr Gln Ser Glu Asn Ser Cys Thr His
             20                  25                  30

Phe Pro Gly Asn Leu Pro Asn Met Leu Arg Asp Leu Arg Asp Ala Phe
         35                  40                  45

Ser Arg Val Lys Thr Phe Phe Gln Met Lys Asp Gln Leu Asp Asn Leu
 50                  55                  60

Leu Leu Lys Glu Ser Leu Leu Glu Asp Phe Lys Gly Tyr Leu Gly Cys
 65                  70                  75                  80

Gln Ala Leu Ser Glu Met Ile Gln Phe Tyr Leu Glu Glu Val Met Pro
                 85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

(2) INFORMATION FOR SEQ ID NO:7:

(i) SEQUENCE CHARACTERISTICS:
        (A) LENGTH: 510 base pairs
        (B) TYPE: nucleic acid
        (C) STRANDEDNESS: single -continued

```
        (D) TOPOLOGY: linear (ii) MOLECULE TYPE: cDNA (ix) FEATURE:
        (A) NAME/KEY: mat_peptide
        (B) LOCATION: 64..510

(xi) SEQUENCE DESCRIPTION: SEQ ID NO:7:

ATGYTNGTNA AYTTYATHYT NMGNTGYGGN YTNYTNYTNG TNACNYTNWS NYTNGCNATH     60

GCNAARCAYC ARWSNWSNTT YACNAARWSN TGYTAYCCNM GNGGNACNYT NWSNCARGCN    120

GTNGAYGCNY TNTAYATHAA RGCNGCNTGG YTNAARGCNA CNATHCCNGA RGAYMGNATH    180

AARAAYATHM GNYTNYTNAA RAARAARACN AARAARCART TYATGAARAA YTGYCARTTY    240

CARGARCARY TNYTNWSNTT YTTYATGGAR GAYGTNTTYG GNCARYTNCA RYTNCARGGN    300

TGYAARAARA THMGNTTYGT NGARGAYTTY CAYACNYTNM GNCARAARYT NWSNCAYTGY    360

ATHWSNTGYG CNWSNWSNGC NMGNGARATG AARWSNATHA CNMGNATGAA RMGNATHTTY    420

TAYMGNATHG GNAAYAARGG NATHTAYAAR GCNATHWSNG ARYTNGAYAT HYTNYTNWSN    480

TGGATHAARA ARYTNYTNGA RWSNWSNCAR                                     510
```

DNA ENCODING IL-10-LIKE HOMOLOGUE; RELATED REAGENTS

This filing is a conversion of a provisional patent application USSN 60/027,368, filed Sep. 23, 1996, which is incorporated herein by reference, to a regular utility Patent Application.

FIELD OF THE INVENTION

The present invention pertains to compositions related to proteins which function in controlling biology and physiology of mammalian cells, e.g., cells of a mammalian immune system. In particular, it provides purified genes, proteins, antibodies, and related reagents useful, e.g., to regulate activation, development, differentiation, and function of various cell types, including hematopoietic cells.

BACKGROUND OF THE INVENTION

Recombinant DNA technology refers generally to the technique of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (MRNA) coding for a desired protein product. The carrier is frequently a plasmid having the capacity to incorporate cDNA for later replication in a host and, in some cases, actually to control expression of the cDNA and thereby direct synthesis of the encoded product in the host.

For some time, it has been known that the mammalian immune response is based on a series of complex cellular interactions, called the "immune network". Recent research has provided new insights into the inner workings of this network. While it remains clear that much of the response does, in fact, revolve around the network-like interactions of lymphocytes, macrophages, granulocytes, and other cells, immunologists now generally hold the opinion that soluble proteins, known as lymphokines, cytokines, or monokines, play a critical role in controlling these cellular interactions. Thus, there is considerable interest in the isolation, characterization, and mechanisms of action of cell modulatory factors, an understanding of which will lead to significant advancements in the diagnosis and therapy of numerous medical abnormalities, e.g., immune system disorders.

Lymphokines apparently mediate cellular activities in a variety of ways. They have been shown to support the proliferation, growth, and differentiation of pluripotential hematopoietic stem cells into vast numbers of progenitors comprising diverse cellular lineages making up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types.

Another important cell lineage is the mast cell (which has not been positively identified in all mammalian species), which is a granule-containing connective tissue cell located proximal to capillaries throughout the body. These cells are found in especially high concentrations in the lungs, skin, and gastrointestinal and genitourinary tracts. Mast cells play a central role in allergy-related disorders, particularly anaphylaxis as follows: when selected antigens crosslink one class of immunoglobulins bound to receptors on the mast cell surface, the mast cell degranulates and releases mediators, e.g., histamine, serotonin, heparin, and prostaglandins, which cause allergic reactions, e.g., anaphylaxis.

Research to better understand and treat various immune disorders has been hampered by the general inability to maintain cells of the immune system in vitro. Immunologists have discovered that culturing these cells can be accomplished through the use of T-cell and other cell supernatants, which contain various growth factors, including many of the lymphokines.

The gene encoding IL-10, originally designated Cytokine Synthesis Inhibitiory Factor (CSIF), was isolated in the 1980's. See, e.g., Mosmann, et al., U.S. Pat. No. 5,231,012. Since then, much has been learned of the biology and physiology mediated by the cytokine. See, e.g., de Vries and de Waal Malefyt (1995) Interleukin-10 Landes Co., Austin, Tex.

From the foregoing, it is evident that the discovery and development of new lymphokines, e.g., related to IL-10, could contribute to new therapies for a wide range of degenerative or abnormal conditions which directly or indirectly involve the immune system and/or hematopoietic cells. In particular, the discovery and development of lymphokines which enhance or potentiate the beneficial activities of known lymphokines would be highly advantageous. The present invention provides new interleukin compositions and related compounds, and methods for their use.

SUMMARY OF THE INVENTION

The present invention is directed to mammalian, e.g., rodent, canine, feline, primate, interleukin-XX (IL-XX) and its biological activities. It includes nucleic acids coding for polypeptides themselves and methods for their production and use. The nucleic acids of the invention are characterized, in part, by their homology to cloned complementary DNA (cDNA) sequences enclosed herein, and/or by functional assays for IL-10-like activities applied to the polypeptides, which are typically encoded by these nucleic acids. Methods for modulating or intervening in the control of an immune response are provided.

The present invention is based, in part, upon the discovery of a new cytokine exhibiting high sequence similarity to cellular IL-10. In particular, it provides a gene encoding a protein whose mature size is about 150 amino acids, which is expressed in virally transformed cells, and certain tissues, e.g., kidney, and possibly lung and liver. Functional equivalents exhibiting significant sequence homology will be available from other mammalian, e.g., mouse and rat, and non-mammalian species.

More particularly, the present invention provides a substantially pure or recombinant IL-XX protein or peptide fragment thereof. Various embodiments include an antigenic protein or peptide selected from a protein or peptide from a warm blooded animal selected from the group of birds and mammals, including a primate; a protein or peptide comprising at least one polypeptide segment of SEQ ID NO: 2; a protein or peptide which exhibits a post-translational modification pattern distinct from natural IL-XX; or a protein or peptide which is capable of co-stimulating a T cell with another signal. The protein or peptide can comprise a fusion protein. Another embodiment is a composition comprising an IL-XX protein or peptide and a pharmaceutically acceptable carrier.

The invention also embraces an antibody which specifically binds a IL-XX protein or peptide, e.g., wherein the IL-XX is a mammalian protein, including a primate; the antibody is raised against a purified IL-XX peptide sequence of SEQ ID NO: 2; the antibody is a monoclonal antibody; or the antibody is labeled. The antibodies also make available a method of purifying an IL-XX protein or peptide from other materials in a mixture comprising contacting the mixture to an anti-IL-XX antibody, and separating bound IL-XX from other materials.

Another aspect of the invention is an isolated or recombinant nucleic acid capable of encoding a full length or mature IL-XX protein or peptide, including a nucleic acid which encodes a sequence of SEQ ID NO: 2; which includes a sequence of SEQ ID NO: 1; or which encodes a sequence from a natural IL-XX. Such nucleic acid embodiments also include an expression or replicating vector.

The invention also provides a kit containing a substantially pure IL-XX or fragment; an antibody or receptor which specifically binds an IL-XX; or a nucleic acid, or its complement, encoding an IL-XX or peptide. This kit also provides methods for detecting in a sample the presence of a nucleic acid, protein, or antibody, comprising testing said sample with such a kit.

The invention also supplies methods of modulating the physiology of a cell comprising contacting said cell with a substantially pure IL-XX or fragment; an antibody or binding partner which specifically binds an IL-XX; or a nucleic acid encoding an IL-XX or peptide. Certain preferred embodiments include a method where the cell is a T cell and the modulating of physiology is activation of the T cell or apoptosis of the T cell; or where the cell is in a tissue and/or in an organism.

Also provided are a method of expressing an IL-XX peptide by expressing a nucleic acid encoding an IL-XX polypeptide. The invention also provides a cell, tissue, organ, or organism comprising a nucleic acid encoding an IL-XX peptide.

The invention also provides a recombinant nucleic acid comprising sequence at least about 70% identity over a stretch of at least about 30 nucleotides to an IL-XX nucleic acid sequence of SEQ ID NO: 1, useful, e.g., as a probe or PCR primer for a related gene. Another embodiment further encodes a polypeptide comprising at least about 60% identity over a stretch of at least about 20 amino acids to an IL-XX sequence of SEQ ID NO: 2.

The invention further provides a method of treating a patient having an abnormal immune response by administering an effective dose of an antibody or binding partner specific for IL-XX; an IL-XX protein or polypeptide; or a nucleic acid encoding an IL-XX peptide. The abnormal immune response is characterized by a T cell immune deficiency; chronic inflammation; or tissue rejection.

DETAILED DESCRIPTION OF THE PREFERRED EMBODIMENTS

All references cited herein are incorporated herein by reference to the same extent as if each individual publication or patent application was specifically and individually indicated to be incorporated by reference.

| OUTLINE | | |
|---|---|---|
| I. | General | |
| II. | Purified IL-XX | |
| | A. | physical properties |
| | B. | biological properties |
| III. | Physical Variants | |
| | A. | sequence variants, fragments |
| | B. | post-translational variants |
| | 1. | glycosylation |
| | 2. | other |
| IV. | Functional Variants | |
| | A. | analogs, fragments |
| | 1. | agonists |
| | 2. | antagonists |
| | B. | mimetics |
| | 1. | protein |
| | 2. | chemicals |
| | C. | species variants |
| V. | Antibodies | |
| | A. | polyclonal |
| | B. | monoclonal |
| | C. | fragments, binding compositions |
| VI. | Nucleic Acids | |
| | A. | matural isolates; methods |
| | B. | synthetic genes |
| | C. | methods to isolate |
| VII. | Making IL-XX, mimetics | |
| | A. | recomhinant methods |
| | B. | synthetic methods |
| | C. | natural purification |
| VIII. | Uses | |
| | A. | diagnostic |
| | B. | therapeutic |
| IX. | Kits | |
| | A. | nucleic acid reagents |
| | B. | protein reagents |
| | C. | antibody reagents |
| X. | Isolating IL-XX receptor | |

The present invention provides amino acid sequences and DNA sequences encoding various mammalian proteins which are cytokines, e.g., which are secreted molecules which can mediate a signal between immune or other cells. See, e.g., Paul (1994) *Fundamental Immunology*, Raven Press, N.Y. The full length cytokines, and fragments, or antagonists will be useful in physiological modulation of cells expressing a receptor. It is likely that IL-XX has either stimulatory or inhibitory effects on T-cells, B-cells, natural killer (NK) cells, macrophages, dentritic cells, hematopoietic progenitors, etc. The proteins will also be useful as antigens, e.g., immunogens, for raising antibodies to various epitopes on the protein, both linear and conformational epitopes.

A cDNA encoding IL-XX was isolated from a virally infected cell. The IL-XX cDNA contains a stretch of 510 bp in length and contained one large open reading frame encoding a small soluble cytokine-like protein. Structural features include an N-terminal leader sequence of about 21 amino acids, though the natural cleavage site may vary with cell, and may be on either side by a few residues. See Table 1 and SEQ. ID. NO: 1 and 2. IL-XX exhibits structural motifs characteristic of a member of the short chain cytokines. Compare, e.g., IL-XX, cellular IL-10s from mouse and human, EBV viral IL-10, and the Equine herpesvirus IL-10. See Table 2. Table 3 represents nucleotide sequences which encode the protein sequence.

TABLE 1

Human IL-XX nucleotide and predicted amino-acid sequence. Predicted leader sequence ends after about 21 amino acids, though natural boundaries may be different, also depending upon cell type. The standard domain boundaries to helix A correspond to residues about 16-39; α1 from about 47-55; helix B from about 81-100; α2 from about 110-123; and helix D from about 125-150. See SEQ ID NO: 1 and 2.

```
CTGTGAGTGA CACACGCTGA GTGGGGTGAA GGGAA ATG CTG GTG AAT TTC ATT         53
                                       Met Leu Val Asn Phe Ile
                                       -21 -20

TTG AGG TGT GGG TTG CTG TTA GTC ACT CTG TCT CTT GCC ATT GCC AAG        101
Leu Arg Cys Gly Leu Leu Leu Val Thr Leu Ser Leu Ala Ile Ala Lys
-15              -10              -5                           1

CAC AAG CAA TCT TCC TTC ACC AAA AGT TGT TAC CCA AGG GGA ACA TTG        149
His Lys Gln Ser Ser Phe Thr Lys Ser Cys Tyr Pro Arg Gly Thr Leu
              5                  10                  15

TCC CAA GCT GTT GAC GCT CTC TAT ATC AAA GCA GCA TGG CTC AAA GCA        197
Ser Gln Ala Val Asp Ala Leu Tyr Ile Lys Ala Ala Trp Leu Lys Ala
            20                  25                  30

ACG ATT CCA GAA GAC CGC ATA AAA AAT ATA CGA TTA TTA AAA AAG AAA        245
Ser Ile Pro Glu Asp Arg Ile Lys Asn Ile Arg Leu Leu Lys Lys Lys
      35                  40                  45

ACA AAA AAG CAG TTT ATG AAA AAC TGT CAA TTT CAA GAA CAG CTT CTG        293
Thr Lys Lys Gln Phe Met Lys Asn Cys Gln Phe Gln Glu Gln Leu Leu
50                  55                  60                  65

TCC TTC TTC ATG GAA GAC GTT TTT GGT CAA CTG CAA TTG CAA GGC TGC        341
Ser Phe Phe Met Glu Asp Val Phe Gly Gln Leu Gln Leu Gln Gly Cys
                  70                  75                  80

AAG AAA ATA CGC TTT GTG GAG GAC TTT CAT AGC CTT AGG CAG AAA TTG        389
Lys Lys Ile Arg Phe Val Glu Asp Phe His Ser Leu Arg Gln Lys Leu
                85                  90                  95

AGC CAC TGT ATT TCC TGT CGT TCA TCA GCT AGA GAG ATG AAA TCC ATT        437
Ser His Cys Ile Ser Cys Arg Ser Ser Ala Arg Glu Met Lys Ser Ile
            100                 105                 110

ACC AGG ATG AAA AGA ATA TTT TAT AGG ATT GGA AAC AAA GGA ATC TAC        485
Thr Arg Met Lys Arg Ile Phe Tyr Arg Ile Gly Asn Lys Gly Ile Tyr
115                 120                 125

AAA GCC ATC AGT GAA CTG GAT ATT CTT CTT TCC TGG ATT AAA AAA TTA        533
Lys Ala Ile Ser Glu Leu Asp Ile Leu Leu Ser Trp Ile Lys Lys Leu
130                 135                 140

TTG GAA AGC AGT CAG TAAACCAAAG CCAAGTACAT TGATTTTACA GTTATTTTGA        588
Leu Glu Ser Ser Gln
              150

AATACAATAA GAACTGCTAG AAATATGTTT ATAACAGTCT ATTTCTTTTA AAACTTTTT      648

AACATAATAC TGACGGCATG TTAGGTGATT CAGAATAGAC AAGAAGGATT TAGTAAATTA      708

ACGTTTTGGA TATAAGTTGT CACTAATTTG CACATTTTCT GTGTTTTCAA ATAATGTTTC      768

CATTCTGAAC ATGTTTTGTC ATTCACAAGT ACATTGTGTC AACTTAATTT AAAGTATGTA      828

ACCTGAATTA ACTCGTGTAA TATTTGTGTG TGGAGTGGGA TGTGGGGGGT GGAGGGGGAA      888

TGACAGATTT CTGGAATGCA ATGTAATGTT ACTGAGACTT AAATAGATGT TATGTATATG      948

ATTGTCTGTT TAAGTGTTTG AAAATTGTTA ATTATGCCCA GTGTGAACTT AGTACTTAAC     1008

ACATTTTGAT TTTAATTAAA TAAATTGGGT TTCCTTCTCA AAAAAAAAAA AAAAAAAAA     1068

AAAAAAAA
```

TABLE 2

Comparison of various IL-10 embodiments compared to IL-XX. First group is signal sequences, which are not aligned. See SEQ ID NO:2–6.

| | |
|---|---|
| MFRASLLCCLVLLAGVWA | Equine Herpes Virus (EHV) |
| MERRLVVTLQCLVLLYLAPECGG | Epstein Barr Virus (EBV) |
| MPGSALLCCLLLLTGMRI | moIL-10 |
| MHSSALLCCLVLLTGVRA | huIL-10 |
| MLVNFILRCGLLLVTLSLAIA | huIL-XX |
| | |
| DNKYDSESGDDCPTLPTSLPHMLHEL-RAAFSRVKTFFQMKDQL | EHV |
| TDQCDNFPQMLRDLRDAFSRVKT-FFQTKDEV | EBV |
| SRGQYSREDNNCTHFPVGQSHMLLELR-TAFSQVKTFFQTKDQL | moIL-10 |
| SPGQGTQSENSCTHFPGNLPNMLRDL-RDAFSRVKTFFQMKDQL | huIL-10 |
| KHKQSSFTKSC YPRGTLSQAVDALYI-KAAWLKATIPEDRIK | huIL-XX |
| | |
| DNMLLDGSLLEDFKGYLGCQALSEMIQ-FYLEEVMPQAENHSTDQ | EHV |
| DNLLLKESLLEDFKGYLGCQALSEMIQ-FYLEEVMPQAENQDPE | EBV |
| DNILLTDSLMQDFKGYLGCQALSEMIQ-FYLVEVMPQAEKHGPE | moIL-10 |
| DNLLLKESLLEDFKGYLGCQALSEMIQ-FYLEEVMPQAENQDPD | huIL-10 |
| NIRLLKKKTKKQFM KNCQFQEQLLSFFMEDVFGQLQLQG | huIL-XX |
| | |
| EKDKVNSLGEKLKTLRVRLRRCHRFLPCENK | EHV |
| AKDHVNSLGENLKTLRLRLRRCHRFLPCENK | EBV |
| IKEHLNSLGEKLKTLRMRLRRCHRFLPCENK | moIL-10 |
| IKAHVNSLGENLKTLRLRLRRCHRFLPCENK | huIL-10 |
| CKKIRFVEDFHTLRQKLSHCIS CASS | huIL-XX |
| | |
| SKAVEQVKSAFSKLQEKGVYKAMSEFDI-FINYIEAYMTTKMKN | EHV |
| SKAVEQIKNAFNKLQEKGIYKAMSEFDI-FINYIEAYMTIKAR | EBV |
| SKAVEQVKSDFNKLQDQGVYKAMNEFDI-FINCIEAYMMIKMKS | mIL-10 |
| SKAVEQVKNAFNKLQEKGIYKAMSEFDI-FINYIEAYMTMKIRN | huIL-10 |
| AREMKSITRMKRIFYRIGNKGIYKAISELDILLSWIKKLLESSQ | huIL-XX |

TABLE 3

Reverse Translation of the amino acid sequence of human IL-XX, e.g., those nucleotide sequences which encode said protein. See SEQ ID NO: 7.

```
ATG YTN GTN AAY TTY ATH YTN MGN TGY G-
GN YTN YTN YTN GTN ACN
YTN WSN YTN GCN ATH GCN  (signal)
AAR CAY CAR WSN WSN TTY ACN AAR WSN T-
GY TAY CCN MGN GGN ACN
YTN WSN CAR GCN GTN GAY GCN YT-
N TAY ATH AAR GCN GCN TGG YTN
AAR GCN ACN ATH CCN GAR GAY MG-
N ATH AAR AAY ATH MGN YTN YTN
AAR AAR AAR ACN AAR AAR CAR TTY AT-
G AAR AAY TGY CAR TTY CAR
GAR CAR YTN YTN WSN TTY TTY ATG GAR-
 GAY GTN TTY GGN CAR YTN
CAR YTN CAR GGN TGY AAR AAR ATH MGN T-
TY GTN GAR GAY TTY CAY
ACN YTN MGN CAR AAR YTN WSN CAY T-
GY ATH WSN TGY GCN WSN WSN
GCN MGN GAR ATG AAR WSN ATH ACN MG-
N ATG AAR MGN ATH TTY TAY
MGN ATH GGN AAY AAR GGN ATH-
 TAY AAR GCN ATH WSN GAR YTN GAY
ATH YTN YTN WSN TGG ATH AAR AAR YTN Y-
TN GAR WSN WSN CAR
```

By Northern analysis, it is clear that IL-XX is expressed in virus transformed T cell lines from primates, including humans. RT PCR has indicated that IL-XX is also expressed in PHA activated PBMC, and in Jurkat and SupTi1 cell lines.

Hybridization to mRNA indicates expression in human kidney, and is detected in lung and liver tissue. The transcript size is about 1.0–1.2 kb, and the gene has been mapped to human chromosome 12q15. Transcripts for IL-XX have not been detected by Northern analysis in PHA activated PBMC, Jurkat cells, owl monkey kidney (OMK) cells, and human herpes infected OMK cells; and by RT PCR in HeLa cells, and the EBV-free B cell line BJA-B.

The structural homology of IL-XX to the related IL-10 proteins suggests similar function of this molecule. IL-XX, as a small chain cytokine, likely mediates immune functions via a receptor of the class of cytokine receptors, possibly even sharing parts or all of the functional IL-10 receptor complex.

IL-XX agonists, or antagonists, may also act as functional or receptor antagonists, e.g., which block IL-10 binding to its receptor, or mediating the opposite actions. Thus, IL-XX, or its antagonists, may be useful in the treatment of abnormal immune disorders, e.g., T cell immune deficiencies, chronic inflammation, or tissue rejection.

The natural antigens are capable of mediating various biochemical responses which lead to biological or physiological responses in target cells. The embodiment characterized herein is from human, but other primate, or other species counterparts are expected to exist in nature. Additional sequences for proteins in other mammalian species, e.g., primates, canines, felines, and rodents, should also be available. See below. The descriptions below are directed, for exemplary purposes, to a human IL-XX, but are likewise applicable to related embodiments from other species.

The human IL-XX protein exhibits structural features characteristic of short chain cytokines.

II. Purified IL-XX

Human IL-XX amino acid sequence is shown in SEQ ID NO: 2. These amino acid sequences, provided amino to carboxy, are important in providing sequence information in the cytokine allowing for distinguishing the protein antigen from other proteins and exemplifying numerous variants. Moreover, the peptide sequences allow preparation of peptides to generate antibodies to recognize such segments, and nucleotide sequences allow preparation of oligonucleotide probes, both of which are strategies for detection or isolation, e.g., cloning, of genes encoding such sequences.

As used herein, the term "human IL-XX" shall encompass, when used in a protein context, a protein having amino acid sequence shown in SEQ ID NO: 2, or a significant fragment of such a protein, or another highly homologous protein derived from human, as distinguished from human IL-10. Binding components, e.g., antibodies, typically bind to an IL-XX with high affinity, e.g., at least about 100 nM, usually better than about 30 nM, preferably better than about 10 nM, and more preferably at better than about 3 nM. Homologous proteins would be found in mammalian species other than human, e.g., other primates or rodents. Non-mammalian species should also possess structurally or functionally related genes and proteins, e.g., birds or amphibians.

The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids, e.g., 35, 40, 45, 50, etc. Such fragments may have ends which begin and/or end at virtually all positions, e.g., beginning at residues 1, 2, 3, etc., and ending at, e.g., 150, 149, 148, etc., in all combinations. Particularly interesting peptides have ends corresponding to structural domain boundaries, e.g., helices A, B, C, and/or D. See Table 1. Note that the sequence of IL-XX exhibits particular identity to cellular IL-10 in the region from residue 126–137, and the other regions exhibit greater extents of IL-XX specific sequence. Seemingly important residues are those shared among all of the four entities in Table 3.

The term "binding composition" refers to molecules that bind with specificity to IL-XX, e.g., in an antibody-antigen interaction. It also includes compounds, e.g., proteins, which specifically associate with IL-XX, including in a natural physiologically relevant protein-protein interaction, either covalent or non-covalent. The molecule may be a polymer, or chemical reagent. A functional analog may be a protein with structural modifications, or it may be a molecule which has a molecular shape which interacts with the appropriate binding determinants. The compounds may serve as agonists or antagonists of a receptor binding interaction, see, e.g., Goodman, et al. (eds.) (1990) *Goodman & Gilman's: The Pharmacological Bases of Therapeutics* (8th ed.), Pergamon Press.

Substantially pure typically means that the protein is free from other contaminating proteins, nucleic acids, or other biologicals derived from the original source organism. Purity may be assayed by standard methods, typically by weight, and will ordinarily be at least about 40% pure, generally at least about 50% pure, often at least about 60% pure, typically at least about 80% pure, preferably at least about 90% pure, and in most preferred embodiments, at least about 95% pure. Carriers or excipients will often be added.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. For diagnostic purposes, the temperature will usually be about room temperature or warmer, but less than the denaturation temperature of components in the assay. For therapeutic purposes, the temperature will usually be body temperature, typically about 37° C. for humans and mice, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents.

The solvent and electrolytes will usually be a biologically compatible buffer, of a type used for preservation of biological activities, and will usually approximate a physiological aqueous solvent. Usually the solvent will have a neutral pH, typically between about 5 and 10, and preferably about 7.5. On some occasions, one or more detergents will be added, typically a mild non-denaturing one, e.g., CHS (cholesteryl hemisuccinate) or CHAPS (3-[3-cholamidopropyl)dimethylammonio]-1-propane sulfonate), or a low enough concentration as to avoid significant disruption of structural or physiological properties of the protein.

III. Physical Variants

This invention also encompasses proteins or peptides having substantial amino acid sequence identity with the amino acid sequence of the IL-XX antigen. The variants include species, polymorphic, or allelic variants.

Amino acid sequence homology, or sequence identity, is determined by optimizing residue matches, if necessary, by introducing gaps as required. See also Needleham, et al. (1970) *J. Mol. Biol.* 48:443–453; Sankoff, et al. (1983) Chapter One in *Time Warps String Edits, and Macromolecules: The Theory and Practice of Sequence Comparison*, Addison-Wesley, Reading, Mass.; and software packages from IntelliGenetics, Mountain View, Calif.; and the University of Wisconsin Genetics Computer Group, Madison, Wis. Sequence identity changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. The conservation may apply to biological features, functional features, or structural features. Homologous amino acid sequences are typically intended to include natural polymorphic or allelic and interspecies variations in each respective protein sequence. Typical homologous proteins or peptides will have from 25–100% identity (if gaps can be introduced), to 50–100% identity (if conservative substitutions are included) with the amino acid sequence of the IL-XX. Identity measures will be at least about 35%, generally at least about 40%, often at least about 50%, typically at least about 60%, usually at least about 70%, preferably at least about 80%, and more preferably at least about 90%.

The isolated IL-XX DNA can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, antigenic, or other functional activity. These modified sequences can be used to produce mutant antigens or to enhance expression. Enhanced expression may involve gene amplification, increased transcription, increased translation, and other mechanisms. "Mutant IL-XX" encompasses a polypeptide otherwise falling within the sequence identity definition of the IL-XX as set forth above, but having an amino acid sequence which differs from that of IL-XX as normally found in nature, whether by way of deletion, substitution, or insertion. This generally includes proteins having significant identity with a protein having sequence of SEQ ID NO: 2, and as sharing various biological activities, e.g., antigenic or immunogenic, with those sequences, and in preferred embodiments contain most of the full length disclosed sequences. Full length sequences will typically be preferred, though truncated versions will also be useful, likewise, genes or proteins found from natural sources are typically most desired. Similar concepts apply to different IL-XX proteins, particularly those found in various warm blooded animals, e.g., mammals and birds. These descriptions are generally meant to encompass all IL-XX proteins, not limited to the particular mouse embodiments specifically discussed.

IL-XX mutagenesis can also be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See, e.g., Sambrook, et al. (1989); Ausubel, et al. (1987 and Supplements); and Kunkel, et al. (1987) *Methods in Enzymol.* 154:367–382.

The present invention also provides recombinant proteins, e.g., heterologous fusion proteins using segments from these proteins. A heterologous fusion protein is a fusion of proteins or segments which are naturally not normally fused in the same manner. A similar concept applies to heterologous nucleic acid sequences.

In addition, new constructs may be made from combining similar functional domains from other proteins. For example, target-binding or other segments may be "swapped" between different new fusion polypeptides or fragments.

See, e.g., Cunningham, et al. (1989) *Science* 243:1330–1336; and O'Dowd, et al. (1988) *J. Biol. Chem.* 263:15985–15992.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

IV. Functional Variants

The blocking of physiological response to IL-XXs may result from the competitive inhibition of binding of the ligand to its receptor. IL-XX binding to IL-10 receptor may serve to induce signaling, e.g., send a signal similar to binding by IL-10. Alternatively, IL-XX binding to IL-10 receptor may block IL-10 signaling. An IL-XX antagonist would be expected to have the opposite effect as IL-XX.

In vitro assays of the present invention will often use isolated protein, soluble fragments comprising receptor binding segments of these proteins, or fragments attached to solid phase substrates. These assays will also allow for the diagnostic determination of the effects of either binding segment mutations and modifications, or cytokine mutations and modifications, e.g., IL-XX analogues.

This invention also contemplates the use of competitive drug screening assays, e.g., where neutralizing antibodies to the cytokine, or receptor binding fragments compete with a test compound.

"Derivatives" of IL-XX antigens include amino acid sequence mutants from naturally occuring forms, glycosylation variants, and covalent or aggregate conjugates with other chemical moieties. Covalent derivatives can be prepared by linkage of functionalities to groups which are found in IL-XX amino acid side chains or at the N- or C-termini, e.g., by standard means. See, e.g., Lundblad and Noyes (1988) *Chemical Reagents for Protein Modification*, vols. 1–2, CRC Press, Inc., Boca Raton, Fla.; Hugli (ed.) (1989) *Techniques in Protein Chemistry*, Academic Press, San Diego, Calif.; and Wong (1991) *Chemistry of Protein Conjugation and Cross Linking*, CRC Press, Boca Raton, Fla.

In particular, glycosylation alterations are included, e.g., made by modifying the glycosylation patterns of a polypeptide during its synthesis and processing, or in further processing steps. See, e.g., Elbein (1987) *Ann. Rev. Biochem.* 56:497–534. Also embraced are versions of the peptides with the same primary amino acid sequence which have other minor modifications, including phosphorylated amino acid residues, e.g., phosphotyrosine, phosphoserine, or phosphothreonine.

Fusion polypeptides between IL-XXs and other homologous or heterologous proteins are also provided. Many cytokine receptors or other surface proteins are multimeric, e.g., homodimeric entities, and a repeat construct may have various advantages, including lessened susceptibility to proteolytic cleavage. Typical examples are fusions of a reporter polypeptide, e.g., luciferase, with a segment or domain of a protein, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, yeast alpha mating factor, and detection or purification tags such as a FLAG sequence of His6 sequence. See, e.g., Godowski, et al. (1988) *Science* 241:812–816.

Fusion peptides will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), vols. 1–3, Cold Spring Harbor Laboratory; and Ausubel, et al. (eds..) (1993) *Current Protocols in Molecular Biology*, Greene and Wiley, NY. Techniques for synthesis of polypeptides are described, e.g., in Merrifield (1963) *J. Amer. Chem. Soc.* 85:2149–2156; Merrifield (1986) *Science* 232: 341–347; Atherton, et al. (1989) *Solid Phase Peptide Synthesis: A Practical Approach*, IRL Press, Oxford; and Grant (1992) *Synthetic Peptides: A User's Guide*, W. H. Freeman, NY. Refolding methods may be applicable to synthetic proteins.

This invention also contemplates the use of derivatives of IL-XX proteins other than variations in amino acid sequence or glycosylation. Such derivatives may involve covalent or aggregative association with chemical moieties or protein carriers. Covalent or aggregative derivatives will be useful as immunogens, as reagents in immunoassays, or in purification methods such as for affinity purification of binding partners, e.g., other antigens. An IL-XX can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-IL-XX antibodies or an alternative binding composition. The IL-XX proteins can also be labeled with a detectable group, e.g., for use in diagnostic assays. Purification of IL-XX may be effected by an immobilized antibody or complementary binding partner, e.g., binding portion of a receptor.

A solubilized IL-XX or fragment of this invention can be used as an immunogen for the production of antisera or antibodies specific for binding. Purified antigen can be used to screen monoclonal antibodies or antigen-binding fragments, encompassing antigen binding fragments of natural antibodies, e.g., Fab, Fab', F(ab)$_2$, etc. Purified IL-XX antigens can also be used as a reagent to detect antibodies generated in response to the presence of elevated levels of the cytokine, which may be diagnostic of an abnormal or specific physiological or disease condition. This invention contemplates antibodies raised against amino acid sequences encoded by nucleotide sequence shown in SEQ ID NO: 1, or fragments of proteins containing it. In particular, this invention contemplates antibodies having binding affinity to or being raised against specific domains, e.g., helices A, B, C, or D.

The present invention contemplates the isolation of additional closely related species variants. Southern and Northern blot analysis will establish that similar genetic entities exist in other mammals. It is likely that IL-XXs are widespread in species variants, e.g., rodents, lagomorphs, carnivores, artiodactyla, perissodactyla, and primates.

The invention also provides means to isolate a group of related antigens displaying both distinctness and similarities in structure, expression, and function. Elucidation of many of the physiological effects of the molecules will be greatly accelerated by the isolation and characterization of additional distinct species or polymorphic variants of them. In particular, the present invention provides useful probes for identifying additional homologous genetic entities in different species.

The isolated genes will allow transformation of cells lacking expression of an IL-XX, e.g., either species types or cells which lack corresponding proteins and exhibit negative background activity. This should allow analysis of the function of IL-XX in comparison to untransformed control cells.

Dissection of critical structural elements which effect the various physiological functions mediated through these antigens is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390.

Intracellular functions would probably involve receptor signaling. However, protein internalization may occur under certain circumstances, and interaction between intracellular components and cytokine may occur. Specific segments of interaction of IL-XX with interacting components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Further study of the expression and control of IL-XX will be pursued. The controlling elements associated with the antigens should exhibit differential physiological, developmental, tissue specific, or other expression patterns. Upstream or downstream genetic regions, e.g., control elements, are of interest.

Structural studies of the IL-XX antigens will lead to design of new antigens, particularly analogs exhibiting agonist or antagonist properties on the molecule. This can be combined with previously described screening methods to isolate antigens exhibiting desired spectra of activities.

V. Antibodies

Antibodies can be raised to various epitopes of the IL-XX proteins, including species, polymorphic, or allelic variants, and fragments thereof, both in their naturally occurring forms and in their recombinant forms. Additionally, antibodies can be raised to IL-XXs in either their active forms or in their inactive forms, including native or denatured versions. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective IL-XXs, or screened for agonistic or antagonistic activity, e.g., mediated through a receptor. Antibodies may be agonsitic or antagonistic, e.g., by sterically blocking binding to a receptor. These monoclonal antibodies will usually bind with at least a $K_D$ of about 1 mM, more usually at least about 300 μm, typically at least about 100 μM, more typically at least about 30 μM, preferably at least about 10 μM, and more preferably at least about 3 μM or better.

The antibodies of this invention can also be useful in diagnostic applications. As capture or non-neutralizing antibodies, they can be screened for ability to bind to the antigens without inhibiting binding to a receptor. As neutralizing antibodies, they can be useful in competitive binding assays. They will also be useful in detecting or quantifying IL-XX protein or its receptors. See, e.g., Chan (ed.) (1987) *Immunology: A Practical Guide,* Academic Press, Orlando, Fla.; Price and Newman (eds.) (1991) *Principles and Practice of Immunoassay,* Stockton Press, N.Y.; and Ngo (ed.) (1988) *Nonisotopic Immunoassay,* Plenum Press, N.Y. Cross absorptions or other tests will identify antibodies which exhibit various spectra of specificities, e.g., unique or shared species specificities.

Further, the antibodies, including antigen binding fragments, of this invention can be potent antagonists that bind to the antigen and inhibit functional binding, e.g., to a receptor which may elicit a biological response. They also can be useful as non-neutralizing antibodies and can be coupled to toxins or radionuclides so that when the antibody binds to antigen, a cell expressing it, e.g., on its surface, is killed. Further, these antibodies can be conjugated to drugs or other therapeutic agents, either directly or indirectly by means of a linker, and may effect drug targeting.

Antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology,* Hoeber Medical Division, Harper and Row, 1969; Landsteiner (1962) *Specificity of Serological Reactions,* Dover Publications, New York; Williams, et al. (1967) *Methods in Immunology and Immunochemistry,* vol. 1, Academic Press, New York; and Harlow and Lane (1988) *Antibodies: A Laboratory Manual,* CSH Press, NY, for descriptions of methods of preparing polyclonal antisera.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual,* CSH Press; Goding (1986) *Monoclonal Antibodies: Principles and Practice* (2d ed.), Academic Press, New York; and particularly in Kohler and Milstein (1975) in *Nature* 256:495–497, which discusses one method of generating monoclonal antibodies.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277, 437; 4,275,149; and 4,366,241. Also, recombinant immunoglobulins may be produced, see Cabilly, U.S. Pat. No. 4,816,567; Moore, et al., U.S. Pat. No. 4,642,334; and Queen, et al. (1989) *Proc. Nat'l Acad, Sci. USA* 86:10029–10033.

The antibodies of this invention can also be used for affinity chromatography in isolating the protein. Columns can be prepared where the antibodies are linked to a solid support. See, e.g., Wilchek et al. (1984) *Meth. Enzymol,* 104:3–55.

Antibodies raised against each IL-XX will also be useful to raise anti-idiotypic antibodies. These will be useful in detecting or diagnosing various immunological conditions related to expression of the respective antigens.

VI. Nucleic Acids

The described peptide sequences and the related reagents are useful in detecting, isolating, or identifying a DNA clone encoding IL-XX, e.g., from a natural source.

Typically, it will be useful in isolating a gene from mammal, and similar procedures will be applied to isolate genes from other species, e.g., warm blooded animals, such as birds and mammals. Cross hybridization will allow isolation of IL-XX from the same, e.g., polymorphic variants, or other species. A number of different approaches should be available to successfully isolate a suitable nucleic acid clone.

The purified protein or defined peptides are useful for generating antibodies by standard methods, as described above. Synthetic peptides or purified protein can be presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual,* Cold Spring Harbor Press.

For example, the specific binding composition could be used for screening of an expression library made from a cell line which expresses an IL-XX. Screening of intracellular expression can be performed by various staining or immunofluorescence procedures. Binding compositions could be used to affinity purify or sort out cells expressing a surface fusion protein.

The peptide segments can also be used to predict appropriate oligonucleotides to screen a library. The genetic code can be used to select appropriate oligonucleotides useful as probes for screening. See, e.g., SEQ ID NO: 1 or 3. In combination with polymerase chain reaction (PCR) techniques, synthetic oligonucleotides will be useful in selecting correct clones from a library. Complementary sequences will also be used as probes, primers, or antisense strands. Various fragments should be particularly useful, e.g., coupled with anchored vector or poly-A complementary PCR techniques or with complementary DNA of other peptides.

This invention contemplates use of isolated DNA or fragments to encode a biologically active corresponding IL-XX polypeptide. In addition, this invention covers isolated or recombinant DNA which encodes a biologically active protein or polypeptide and which is capable of hybridizing under appropriate conditions with the DNA sequences described herein. Said biologically active protein or polypeptide can be an intact antigen, or fragment, and have an amino acid sequence disclosed in, e.g., SEQ ID NO: 2. Further, this invention covers the use of isolated or recombinant DNA, or fragments thereof, which encode proteins which exhibit high identity to an IL-XX or which was isolated using cDNA encoding an IL-XX as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and/or flanking genomic sequences from the originating species.

The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Generally, the nucleic acid will be in a vector or fragment less than about 50 kb, usually less than about 30 kb, typically less than about 10 kb, and preferably less than about 6 kb.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, e.g., products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site.

Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species or polymorphic variants.

A significant "fragment" in a nucleic acid context is a contiguous segment of at least about 17 nucleotides, generally at least about 22 nucleotides, ordinarily at least about 29 nucleotides, more often at least about 35 nucleotides, typically at least about 41 nucleotides, usually at least about 47 nucleotides, preferably at least about 55 nucleotides, and in particularly preferred embodiments will be at least about 60 or more nucleotides, e.g., 67, 73, 81, 89, 95, etc.

A DNA which codes for an IL-XX protein will be particularly useful to identify genes, MRNA, and cDNA species which code for related or similar proteins, as well as DNAs which code for homologous proteins from different species. There are likely homologs in other species, including primates, rodents, canines, felines, and birds. Various IL-XX proteins should be homologous and are encompassed herein. However, even proteins that have a more distant evolutionary relationship to the antigen can readily be isolated under appropriate conditions using these sequences if they are sufficiently homologous. Primate IL-XX proteins are of particular interest.

Recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology*, Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Embryonic Stem Cells: A Practical Approach*, IRL Press, Oxford; and Rosenberg (1992) *J. Clinical Oncology* 10:180–199.

Substantial homology, e.g., identity, in the nucleic acid sequence comparison context means either that the segments, or their complementary strands, when compared, are identical when optimally aligned, with appropriate nucleotide insertions or deletions, in at least about 50% of the nucleotides, generally at least about 58%, ordinarily at least about 65%, often at least about 71%, typically at least about 77%, usually at least about 85%, preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence of IL-XX, e.g., in SEQ ID NO: 1 or 3. Typically, selective hybridization will occur when there is at least about 55% identity over a stretch of at least about 30 nucleotides, preferably at least about 75% over a stretch of about 25 nucleotides, and most preferably at least about 90% over about 20 nucleotides. See, Kanehisa (1984) *Nuc. Acids Res.* 12:203–213. The length of identity comparison, as described, may be over longer stretches, and in certain embodiments will be over a stretch of at least about 17 nucleotides, usually at least about 28 nucleotides, typically at least about 40 nucleotides, and preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., usually in excess of about 37° C., typically in excess of about 55° C., preferably in excess of about 70° C. Stringent salt conditions will ordinarily be less than about 1000 mM usually less than about 400 mM, typically less than about 250 mM, preferably less than about 150 mM, including about 100, 50, or even 20 mM. However, the combination of parameters is much more important than the measure of any single parameter. See, e.g., Wetmur and Davidson (1968) *J. Mol. Biol.* 31:349–370.

IL-XX from other mammalian species can be cloned and isolated by cross-species hybridization of closely related species. Homology may be relatively low between distantly related species, and thus hybridization of relatively closely related species is advisable. Alternatively, preparation of an antibody preparation which exhibits less species specificity may be useful in expression cloning approaches.

VII. Making IL-XX; Mimetics

DNA which encodes the IL-XX or fragments thereof can be obtained by chemical synthesis, screening cDNA libraries, or screening genomic libraries prepared from a wide variety of cell lines or tissue samples. See, e.g., Okayama and Berg (1982) *Mol. Cell. Biol.* 2:161–170; Gubler and Hoffman (1983) *Gene* 25:263–269; and Glover (ed.) (1984) *DNA Cloning: A Practical Approach*, IRL Press, Oxford. Alternatively, the sequences provided herein provide useful PCR primers or allow synthetic or other preparation of suitable genes encoding an IL-XX; including naturally occuring embodiments.

This DNA can be expressed in a wide variety of host cells for the synthesis of a full-length IL-XX or fragments which can in turn, e.g., be used to generate polyclonal or monoclonal antibodies; for binding studies; for construction and expression of modified molecules; and for structure/function studies.

Vectors, as used herein, comprise plasmids, viruses, bacteriophage, integratable DNA fragments, and other vehicles which enable the integration of DNA fragments into the genome of the host. See, e.g., Pouwels, et al. (1985 and Supplements) *Cloning Vectors: A Laboratory Manual*, Elsevier, N.Y.; and Rodriguez, et al. (1988)(eds.) *Vectors: A Survey of Molecular Cloning Vectors and Their Uses*, Buttersworth, Boston, Mass.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression. See, e.g., Rodriguez, et al., Chapter 10, pp. 205–236; Balbas and Bolivar (1990) *Methods in Enzymology* 185:14–37; and Ausubel, et al. (1993) *Current Protocols in Molecular Biology*, Greene and Wiley, NY.

Representative examples of suitable expression vectors include pCDNA1; pCD, see Okayama, et al. (1985) *Mol. Cell Biol.* 5:1136–1142; pMClneo Poly-A, see Thomas, et al. (1987) *Cell* 51:503–512; and a baculovirus vector such as pAC 373 or pAC 610. See, e.g., Miller (1988) *Ann. Rev. Microbiol.* 42:177–199.

It will often be desired to express an IL-XX polypeptide in a system which provides a specific or defined glycosylation pattern. See, e.g., Luckow and Summers (1988) *Bio/Technology* 6:47–55; and Kaufman (1990) *Meth. Enzymol.* 185:487–511.

The IL-XX, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim, Biophys. Acta* 988:427–454; Tse, et al. (1985) *Science* 230:1003–1008; and Brunner, et al. (1991) *J. Cell Biol.* 114:1275–1283.

Now that the IL-XX has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; Bodanszky (1984) *The Principles of Peptide Synthesis*, Springer-Verlag, New York; and Villafranca (ed.) (1991) *Techniques in Protein Chemistry II*, Academic Press, San Diego, Calif.

VIII. Uses

The present invention provides reagents which will find use in diagnostic applications as described elsewhere herein, e.g., in IL-XX mediated conditions, or below in the description of kits for diagnosis.

This invention also provides reagents with significant therapeutic potential. The IL-XX (naturally occurring or recombinant), fragments thereof, and antibodies thereto, along with compounds identified as having binding affinity to IL-XX, should be useful in the treatment of conditions associated with abnormal physiology or development, including inflammatory conditions, either acute or chronic. In particular, modulation of physiology of lymphoid cells will be achieved by appropriate therapeutic treatment using the compositions provided herein. For example, a disease or disorder associated with abnormal expression or abnormal signaling by an IL-XX should be a likely target for an agonist or antagonist. The new cytokine should play a role in regulation or development of hematopoietic cells, e.g., lymphoid or myeloid cells, which affect immunological responses, e.g., inflammation and/or autoimmune disorders.

In particular, the cytokine should mediate, in various contexts, cytokine synthesis by the cells, proliferation, etc.

Conversely, antagonists of IL-XX, such as mutein variants of a naturally occurring form of IL-XX or blocking antibodies, may provide a selective and powerful way to block immune responses, e.g., in situations as inflammatory or autoimmune responses, including rheumatoid arthritis, systemic lupus erythematosis (SLE), Hashimoto's autoimmune thyroiditis, as well as acute and chronic inflammatory responses, e.g., inflammatory bowel disease. See also Samter, et al. (eds) *Immunological Diseases* vols. 1 and 2, Little, Brown and Co. Modulated cytokine release by the naturally occurring secreted form of IL-XX, which can be produced in large quantities by recombinant methods, or by blocking antibodies, should be regulatable by reagents made available herein, e.g., in a transplantation rejection situation.

In addition, certain combination compositions would be useful, e.g., with other modulators of inflammation. Such other molecules may include steroids, other versions of IL-10, including cellular species variants, or viral IL-10s, e.g., EBV or EHV, and all of their respective antagonists.

Various abnormal conditions are known in each of the cell types shown to produce IL-XX mRNA by Northern blot analysis. See Berkow (ed.) *The Merck Manual of Diagnosis and Therapy*, Merck & Co., Rahway, N.J.; Thorn, et al. *Harrison's Principles of Internal Medicine*, McGraw-Hill, N.Y.; and Weatherall, et al. (eds.) *Oxford Textbook of Medicine,* Oxford University Press, Oxford. Many other medical conditions and diseases involve activation by macrophages or monocytes, and many of these will be responsive to treatment by an agonist or antagonist provided herein. See, e.g., Stites and Terr (eds; 1991) *Basic and Clinical Immunology* Appleton and Lange, Norwalk, Conn.; and Samter, et al. (eds) *Immunological Diseases* Little, Brown and Co. These problems should be susceptible to prevention or treatment using compositions provided herein. IL-XX antibodies can be purified and then administered to a patient, veterinary or human. These reagents can be combined for therapeutic use with additional active or inert ingredients, e.g., in conventional pharmaceutically acceptable carriers or diluents, e.g., immunogenic adjuvants, along with physiologically innocuous stabilizers, excipients, or preservatives. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using IL-XX or fragments thereof can be performed to identify compounds having binding affinity to or other relevant biological effects on IL-XX functions, including isolation of associated components. Subsequent biological assays can then be utilized to determine if the compound has intrinsic stimulating activity and is therefore a blocker or antagonist in that it blocks the activity of the cytokine. Likewise, a compound having intrinsic stimulating activity can activate the signal pathway and is thus an agonist in that it simulates the activity of IL-XX. This invention further contemplates the therapeutic use of blocking antibodies to IL-XX as antagonists and of stimulatory antibodies as agonists. This approach should be particularly useful with other IL-XX species variants.

In addition, IL-XX may play a role in leukemogenesis or in viral infections by, e.g., HTLV or herpesviruses. It is induced by infection with herpesvirus saimiri. The herpesvirus also encodes a homolog of the cytokine IL-17 (CTLA-8). Thus, the cytokine, or antagonists, may be useful in anti-tumor therapy. The viral correlation may suggest that the cytokine may be important in viral infection or proliferation processes, or oncology processes, e.g., oncogenic transformation and proliferative conditions, as cancers or leukemias. See, e.g., Thorn, et al. *Harrison's Principles of Internal Medicine,* McGraw-Hill, N.Y.

In addition, the cytokine appears to be barely expressed in kidney cell, and may play a role in that organ's function, e.g., ion exchange or blood pressure regulation. The cytokine may also have water balance functions. The cytokine may have some detectable expression in kidney.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Penn. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index,* Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous or long term administration. See, e.g., Langer (1990) *Science* 249:1527–1533.

IL-XX, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, topical, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa.; Avis, et al. (eds.) (1993) *Pharmaceutical Dosage Forms: Parenteral Medications,* Dekker, New York; Lieberman, et al. (eds.) (1990) *Pharmaceutical Dosage Forms: Tablets,* Dekker, New York; and Lieberman, et al. (eds.) (1990) *Pharmaceutical Dosage Forms: Disperse Systems,* Dekker, New York. The therapy of this invention may be combined with or used in association with other agents, e.g., other types of IL-10s, or their respective antagonists.

Both the naturally occurring and the recombinant form of the IL-XXs of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate. The development of suitable assays can be greatly facilitated by the availability of large amounts of purified, soluble IL-XX as provided by this invention.

Other methods can be used to determine the critical residues in the IL-XX-IL-XX receptor interactions. Mutational analysis can be performed, e.g., see Somoza, et al. (1993) *J. Exptl. Med.* 178:549–558, to determine specific residues critical in the interaction and/or signaling. However, residues in the A and D helices are likely to be most important in receptor interaction.

For example, antagonists can normally be found once the antigen has been structurally defined, e.g., by tertiary structure data. Testing of potential interacting analogues is now possible upon the development of highly automated assay methods using a purified IL-XX. In particular, new agonists and antagonists will be discovered by using screening techniques described herein. Of particular importance are compounds found to have a combined binding affinity for a spectrum of IL-XX molecules, e.g., compounds which can serve as antagonists for species variants of IL-XX.

One method of drug screening utilizes eukaryotic or prokaryotic host cells which are stably transformed with recombinant DNA molecules expressing an IL-XX. Cells may be isolated which express an IL-XX in isolation from other molecules. Such cells, either in viable or fixed form, can be used for standard binding partner binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses.

Another technique for drug screening involves an approach which provides high throughput screening for compounds having suitable binding affinity to an IL-XX and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified IL-XX, and washed. The next step involves detecting bound IL-XX.

Rational drug design may also be based upon structural studies of the molecular shapes of the IL-XX and other effectors or analogues. Effectors may be other proteins which mediate other functions in response to binding, or other proteins which normally interact with IL-XX, e.g., a receptor. One means for determining which sites interact with specific other proteins is a physical structure determination, e.g., x-ray crystallography or 2 dimensional NMR techniques. These will provide guidance as to which amino acid residues form molecular contact regions, as madeled, e.g., against cellular IL-10. For a detailed description of protein structural determination, see, e.g., Blundell and Johnson (1976) *Protein Crystallography,* Academic Press, New York.

IX. Kits

This invention also contemplates use of IL-XX proteins, fragments thereof, peptides, and their fusion products in a variety of diagnostic kits and methods for detecting the presence of another IL-XX or binding partner. Typically the kit will have a compartment containing either a defined IL-XX peptide or gene segment or a reagent which recognizes one or the other, e.g., IL-XX fragments or antibodies.

A kit for determining the binding affinity of a test compound to an IL-XX would typically comprise a test compound; a labeled compound, for example a binding partner or antibody having known binding affinity for IL-XX; a source of IL-XX (naturally occurring or recombinant); and a means for separating bound from free labeled compound, such as a solid phase for immobilizing the molecule. Once compounds are screened, those having suitable binding affinity to the antigen can be evaluated in suitable biological assays, as are well known in the art, to determine whether they act as agonists or antagonists to the IL-XX signaling pathway. The availability of recombinant IL-XX polypeptides also provide well defined standards for calibrating such assays.

A preferred kit for determining the concentration of, e.g., an IL-XX in a sample would typically comprise a labeled compound, e.g., binding partner or antibody, having known binding affinity for the antigen, a source of cytokine (naturally occurring or recombinant) and a means for separating the bound from free labeled compound, e.g., a solid phase for immobilizing the IL-XX. Compartments containing reagents, and instructions, will normally be provided.

Antibodies, including antigen binding fragments, specific for the IL-XX or fragments are useful in diagnostic applications to detect the presence of elevated levels of IL-XX and/or its fragments. Such diagnostic assays can employ lysates, live cells, fixed cells, immunofluorescence, cell cultures, body fluids, and further can involve the detection of antigens related to the antigen in serum, or the like. Diagnostic assays may be homogeneous (without a separation step between free reagent and antigen-binding partner complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. See, e.g., Van Vunakis, et al. (1980) *Meth Enzymol.* 70:1–525; Harlow and Lane (1980) *Antibodies: A Laboratory Manual,* CSH Press, NY; and Coligan, et al. (eds.) (1993) *Current Protocols in Immunology,* Greene and Wiley, NY.

Anti-idiotypic antibodies may have similar use to diagnose presence of antibodies against an IL-XX, as such may be diagnostic of various abnormal states. For example, overproduction of IL-XX may result in production of various immunological reactions which may be diagnostic of abnormal physiological states, particularly in proliferative cell conditions such as cancer or abnormal activation or differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or binding partner, or labeled IL-XX is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the binding partner, test compound, IL-XX, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free IL-XX, or alternatively the bound from the free test compound. The IL-XX can be immobilized on various matrixes followed by washing. Suitable matrixes include plastic such as an ELISA plate, filters, and beads. See, e.g., Coligan, et al. (eds.) (1993) *Current Protocols in Immunology,* Vol. 1, Chapter 2, Greene and Wiley, NY. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications. Another diagnostic aspect of this invention involves use of oligonucleotide or polynucleotide sequences taken from the sequence of an IL-XX. These sequences can be used as probes for detecting levels of the IL-XX message in samples from patients suspected of having an abnormal condition, e.g., inflammatory or autoimmune. Since the cytokine may be a marker or mediator for activation, it may be useful to determine the numbers of activated cells to determine, e.g., when additional therapy may be called for, e.g., in a preventative fashion before the effects become and progress to significance. The preparation of both RNA and DNA nucleotide sequences, the labeling of the sequences, and the preferred size of the sequences has received ample description and discussion in the literature. See, e.g., Langer-Safer, et al. (1982) *Proc. Nat'l. Acad. Sci.* 79:4381–4385; Caskey (1987) *Science* 236:962–967; and Wilchek et al. (1988) *Anal. Biochem.* 171:1–32.

Diagnostic kits which also test for the qualitative or quantitative expression of other molecules are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97. Other kits may be used to evaluate other cell subsets.

X. Isolating the IL-XX Receptor

Having isolated a ligand of a specific ligand-receptor interaction, methods exist for isolating the receptor. See, Gearing, et al. (1989) *EMBO J.* 8:3667–3676. For example, means to label the IL-XX cytokine without interfering with the binding to its receptor can be determined. For example, an affinity label can be fused to either the amino- or carboxyl-terminus of the ligand, though based on IL-10, the amino-terminus is more likely to succeed. Such label may be a FLAG epitpe tag, or, e.g., an Ig or Fc domain. An expression library can be screened for specific binding of the cytokine, e.g., by cell sorting, or other screening to detect subpopulations which express such a binding component. See, e.g., Ho, et al. (1993) *Proc. Nat'l Acad. Sci. USA* 90:11267–11271; and Liu, et al. (1994) *J. Immunol.* 152:1821–29. Alternatively, a panning method may be used. See, e.g., Seed and Aruffo (1987) Proc. Nat'l Acad. Sci. USA 84:3365–3369.

Protein cross-linking techniques with label can be applied to isolate binding partners of the IL-XX cytookine. This would allow identification of proteins which specifically interact with the cytokine, e.g., in a ligand-receptor like manner.

Early experiments will be performed to determine whether the known IL-10R is involved in response(s) to IL-XX. It is also quite possible that the functional IL-10 receptor complex may share many or all components with an IL-XX receptor complex, either a specific receptor subunit or an accessory receptor subunit.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

EXAMPLES

General Methods

Some of the standard methods are described or referenced, e.g., in Maniatis, et al. (1982) *Molecular Cloning, A Laboratory Manual,* Cold Spring Harbor Laboratory, Cold Spring Harbor Press; Sambrook, et al. (1989) *Molecular Cloning: A Laboratory Manual* (2d ed.), vols 1–3, CSH Press, NY; Ausubel, et al., *Biology,* Greene Publishing Associates, Brooklyn, N.Y.; or Ausubel, et al. (1987 and Supplements) *Current Protocols in Molecular Biology,* Greene and Wiley, New York; Innis, et al. (eds.) (1990) *PCR Protocols: A Guide to Methods and Applications,* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *OIAexpress: The High Level Expression & Protein Purification System* QUIAGEN, Inc., Chatsworth, Calif. Cell culture techniques are described in Doyle, et al. (eds.) (1994) *Cell and Tissue Culture: Laboratory Procedures,* John Wiley and Sons, NY.

FACS analyses are described in Melamed, et al. (1990) *Flow Cytometry and Sorting* Wiley-Liss, Inc., New York, NY; Shapiro (1988) *Practical Flow Cytometry* Liss, New York, N.Y.; and Robinson, et al. (1993) *Handbook of Flow Cytometry Methods* Wiley-Liss, New York, N.Y. Fluorescent labeling of appropriate reagents was performed by standard methods.

EXAMPLE 1

Cloning of Human IL-XX

PBMC were prepared from a healthy human blood donor by conventional Ficoll gradients, as described, e.g., in Coligan, et al. *Current Protocols in Immunology* Greene/ Wiley. Cells from this preparation were stimulated with PHA and cultivated in the presence of IL-2 for several weeks. See, e.g., Fickenscher and Fleckenstein, pp3.45–362, "Generation of human T cell lines using lymphotropic herpesviruses" in Adolph (ed) *Methods in Molecular Genetics: Molecular Virology Techniques Part A* Volume 4, Academic Press, San Diego, Calif. RNA from these PHA-blasts was used later to subtract the normally occurring cDNAs.

Another portion of the PBMC preparation was infected with herpesvirus saimiri C488. See Fickenscher and Fleckenstein, pp345–362, above; and Biesinger, et al. (1992) *Proc. Nat'l Acad. Sci, USA* 89:3116–3119. The infected cells were cultivated in the presence of IL-2 until growth transformation was established (several months). RNA was isolated from the transformed T-cell line, designated 3C (see Fickenscher, et al. (1996) *The Immunologist* 4:41–43), after the cells had been stimulated using 1 ng/ml TPA (Fickenscher, et al. (1996) *J. Virol.* 70:6012–6019) for four hours. RNA was isolated according to Chomczynski and Sacchi (1987) *Anal. Biochem.* 162:156–159. The subtractive cDNA library was prepared with a cDNA subtraction kit (from Clontech, Palo Alto, Calif.).

PCR products were cloned using a TA cloning kit (Invitrogen). The resulting cDNA plasmids were sequenced from both termini on an automated sequencer (Applied Biosystems).

Plasmid ak155 contains a cDNA fragment of 540 nt. There is a single large open reading frame found, starting at nucleotide 12, and ending at nucleotide 524. Termination signals are not found in this partial cDNA. Using 5' and 3' RACE, the remaining fragments of the entire cDNA were cloned. The transcript size is approximately 1.0 to 1.2 kb. Genomic structure analysis indicates that introns exist at or near to between nucleotides 206 and 207, of about 35 nucleotides; between 263 and 264, of about 60 nucleotides; between 398 and 399, of about 1.5 kb; and between 464 and 465, of about 86 nucleotides. The sequences of the short introns have been determined.

The sequence derived from plasmid clone ak155 exhibited distant similarity to IL10s, see Table 3.

EXAMPLE 2

Cellular Expression of Human IL-XX

Because of the sequence similarity to human IL-10, distribution was investigated for similar type cell types. A probe specific for cDNA encoding primate IL-XX is labeled, e.g., by random priming.

IL-XX/ak155 is strongly transcribed in various T-cell lines of human and non-human primates, which have been in-vitro transformed to stable IL-2 dependent growth by herpesvirus saimiri C488. This expression is analysed by Northern blotting. Owl monkey kidney cells (OMK) which are a primate permissive system for the human virus, and virus-infected OMK were negative by Northern blotting. TPA stimulation did not significantly increase IL-XX/ak155 transcript levels in virus-transformed T-cells; and cyclosporin A did not inhibit its expression. Transcription has been confirmed by RT-PCR from transformed human T-cells in 3C and CB15 cells (Biesinger, et al. (1992) *Proc. Nat'l Acad. Sci. USA* 89:3116–3119; Fickenscher and Fleckenstein (1994); and Fickenscher, et al. (1996) *J. Virol.*). It is quite notable that IL-XX is so strongly expressed in herpesvirus saimiri-transformed T-cells, which suggests a role in the transformation mechanism. Expression was also detected in a monkey T cell line 93C488, a cell line from *Saguinus fuscicollis* monkeys that produces virus particles.

By RT-PCR weak transcription was detected in human PHA-activated PBMC, and in T-cell tumor lines like Jurkat (Schneider, et al (1977) *Int. J. Cancer* 19:621–626) and SupTi1 (ATCC CRL-1942; see (1986) *Science* 232:1123–1127; and (1984) *Cancer Res.* 44:5657–5660); and in HTLV-transformed human T cells MT2, C91PL, and HUT102 (which do produce HTLV-Virions; see Popovic, et al. (1984) "Biology of Human T-cell leukemia/lymphoma virus" in Klein (ed.) *Advances in Viral Oncology*, Vol. 4, Raven Press, NY). Thus, a low level of ak155 expression seems typical for human T cells, e.g., leukemia cell lines (Jurkat etc.) and HTLV-transformed cells. Positive signal was detected in macrophages stimulated with IFN-γ and/or LPS, but not after treatment with Protein A expressing cells. No detectable signal was found in HeLa cells, BJA-B ( human B-cell line which does not carry EBV genomes; see Klein, et al. (1974) *Proc. Nat'l Acad. Sci. USA* 71:3283–3286), Tera-2 (human Teratocarcinoma cell line; ATCC HTB106 or CRL-1973), BCBL-1 (HHV8+; an HHV8 virus, which is a close relative to *H. saimiri,* positive EBV negative human B cell line, see Renne, et al. (1996) *Nature Medicine* 2:342–346), Kaposi's sarcoma (HHV8+; clinical sample), cervical carcinoma (HPV16+; clinical sample), thyroid, or kidney. The negative results from BJA-B and Tera-2 may suggest a possibility of specific expression in T cells and macrophages. The HHV8-infected cells like BCBL1 or the tumors did not express AK155, which means that it is therefore specific fo *H. saimiri.* Ak155 transcription was not seen in cervical carcinoma, which suggests that it does not play a significant role in at least one cancers condition.

Using a commercial dot spot mRNA hybridization filter and standard hybridization conditions, faint expression was detected in human kidney, and even fainter in human lung and liver. Expression data from RT-PCR and from the mRNA-dot hybridization should be confirmed by sensitive Northeren or other means. By Northern analysis, negative results were obtained from: PHA-activated PBMC, Jurkat, Owl monkey kidney cells (OMK; ATCC CRL 1556; Daniel, et al. (1976) *In Vitro* 12:290), and OMK infected with herpesvirus saimiri C488. By RT-PCR, Hela cells (epithelial; ATCC CCL-2.1: HeLa229; see (1985) *Am J. Pathol.* 119:361–366) and BJA-B (EBV-free B cell line; see Klein, et al. (1974) *Proc. Nat'l Acad. Sci. USA* 71:3283–3286) gave undetectable expression. Dot blots gave undetectable signals in the following human tissues by MRNA dot spot assay: brain, amygdala, caudate nucleus, cerebellum, cerebral cortex, frontal lobe, hippocampus, medulla oblongata, occipital lobe, putamen, substantia nigra, temporal lobe, thalamus, subthalamic nucleus, spinal cord, heart, aorta, sceletal muscle, colon, bladder, uterus, prostate, stomach, testis, ovary, pancreas, pituitary gland, adrenal gland, thyroid gland, salivary gland, mammary gland, small intestine, spleen, thymus, peripheral leukocytes, lymph node, bone marrow, appendix, trachea, placenta, fetal brain, fetal heart, fetal kidney, fetal liver, fetal spleen, fetal thymus, fetal lung.

EXAMPLE 3

Chromosome Mapping of Human IL-XX ak155 is neither transcribed during lytic infection of OMK cells with herpesvirus saimiri C488, nor can the ak155 sequence be amplified from purified virus DNA. Chromosome mapping is a standard technique. See, e.g., BIOS Laboratories (New Haven, Conn.) and methods for using a mouse somatic cell hybrid panel with PCR. The gene was mapped to the human chrosome 12q15 region.

EXAMPLE 4

Purification of IL-XX Protein

Multiple transfected cell lines are screened for one which expresses the cytokine at a high level compared with other cells. Various cell lines are screened and selected for their favorable properties in handling. Natural IL-XX can be isolated from natural sources, or by expression from a transformed cell using an appropriate expression vector. Early results suggest that the cytokine, after secretion, rebinds to the cell surface. Purification of the expressed protein is achieved by standard procedures, or may be combined with engineered means for effective purification at high efficiency from cell lysates or supernatants. FLAG or His6 segments can be used for such purification features. Alternatively, affinity chromatography may be used with specific antibodies, see below.

EXAMPLE 5

Isolation of Homologous IL-XX Genes

The IL-XX cDNA can be used as a hybridization probe to screen a library from a desired source, e.g., a primate cell cDNA library. Many different species can be screened both for stringency necessary for easy hybridization, and for presence using a probe. Appropriate hybridization conditions will be used to select for clones exhibiting specificity of cross hybridization.

Screening by hybridization using degenerate probes based upon the peptide sequences will also allow isolation of appropriate clones. Alternatively, use of appropriate primers for PCR screening will yield enrichment of appropriate nucleic acid clones.

Similar methods are applicable to isolate either species, polymorphic, or allelic variants. Species variants are isolated using cross-species hybridization techniques based upon isolation of a full length isolate or fragment from one species as a probe.

Alternatively, antibodies raised against human IL-XX will be used to screen for cells which express cross-reactive proteins from an appropriate, e.g., cDNA library. The purified protein or defined peptides are useful for generating antibodies by standard methods, as described above. Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. The resulting antibodies are used for screening, purfication, or diagnosis, as described.

EXAMPLE 6

Preparation of Antibodies Specific for IL-XX

Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. Polyclonal serum, or hybridomas may be prepared. In appropriate situations, the binding reagent is either labeled as described above, e.g., fluorescence or otherwise, or immobilized to a substrate for panning methods.

EXAMPLE 7

Evaluation of Breadth of Biological Functions

The native, recombinant, and fusion proteins would be tested for agonist and antagonist activity in many biological assay systems, e.g., on T-cells, B-cells, NK, macrophages, dentritic cells, hematopoietic progenitors, etc. Because of the IL-10 structural relationship, assays related to IL-10 activity would analysed IL-XX is evaluated for agonist or antagonist activity on transfected cells expressing IL-10 receptor and controls. See, e.g., Ho, et al. (1993) *Proc. Nat'l Acad. Sci. USA* 90, 11267–11271; Ho, et al. (1995) *Mol. Cell. Biol.* 15:5043–5053;and Liu, et al. (1994). *J. Immunol.* 152:1821–1829.

Based, in part, upon the structural homology to IL-10, the IL-XX is evaluated for effect in macrophage/dendritic cell activation and antigen presentation assays, T cell cytokine production and proliferation in response to antigen or allogeneic stimulus. See, e.g., de Waal Malefyt et al. (1991) *J. Exp. Med.* 174:1209–1220; de Waal Malefyt et al. (1991) *J. Exp. Med.* 174:915–924; Fiorentino, et al. (1991) *J. Immunol.* 147, 3815–3822; Fiorentino, et al. (1991) *J. Immunol.* 146:3444–3451; and Groux, et al. (1996) *J. Exp. Med.* 184:19–29.

IL-XX will also be evaluated for effects on NK cell stimulation. Assays may be based, e.g., on Hsu, et al. (1992) *Internat. Immunol.* 4:563–569; and Schwarz, et al. (1994) *J. Immunother.* 16:95–104.

B cell growth and differentiation effects will be analysed, e.g., by the methodology described, e.g., in Defrance, et al. (1992). *J. Exp. Med.* 175:671–682; Rousset, et al (1992) *Proc. Nat'l Acad. Sci. USA* 89:1890–1893; including IgG2 and IgA2 switch factor assays. Note that, unlike COS7 supernatants, NIH3T3 and COP supernatants apparently do not interfere with human B cell assays.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An isolated or recombinant polynucleotide encoding the mature polypeptide of SEQ ID NO: 2.

2. An isolated or recombinant polynucleotide comprising the portion of SEQ ID NO: 1 that encodes the mature polypeptide.

3. A host cell comprising said polynucleotide of claim 1.

4. The polynucleotide of claim 1, that selectively hybridizes, under stringent hybridization wash conditions of at least 55° C. less than 200 mM salt, to SEQ ID NO: 1.

5. The polynucleotide of claim 4, wherein said wash conditions are at least 65° C.

6. The polynucleotide of claim 1, which:

a) is attached to a solid substrate;

b) is detectably labeled;

c) is in a sterile composition;

d) encodes an antigenic polypeptide having at least 12 amino acid residues; or e) is synthetically produced.

7. The polynucleotide of claim 1, that is a variant as a result of the degeneracy of the genetic code.

8. The polynucleotide of claim 2, wherein T is U.

9. An isolated or recombinant polynucleotide encoding a polypeptide that:

a) has a conservative amino acid substitution of a mature polypeptide of SEQ ID NO: 2;

b) is a natural allelic variant of the mature native polypeptide of SEQ ID NO: 2; or c) is a primate species variant of the mature native polypeptide of SEQ ID NO: 2.

10. An expression or replication vector comprising, in operable linkage, said polynucleotide of claim 1.

11. An expression or replication vector comprising, in operable linkage, said polynucleotide of claim 9.

12. The vector of claim 10, comprising the nature polypeptide coding sequence of SEQ ID NO: 1.

13. A host cell comprising said vector of claim 11.

14. A method of producing an antigenic IL-10-like polypeptide comprising expressing said vector of claim 10, thereby producing said polypeptide; and recovering said polypeptide.

15. The vector of claim 11, encoding a polypeptide that specifically binds polyclonal antibodies generated against the mature polypeptide of SEQ ID NO: 2.

16. The vector of claim 10, wherein said polynucleotide selectively hybridizes, under stringent hybridization wash conditions of at least 55° C. and less than 200 mM salt, to SEQ ID NO: 1.

17. The polynucleotide of claim 16, wherein said wash conditions are at least 65° C.

18. The vector of claim 10, that is:

a) a virus; or b) a plasmid.

19. The host cell of claim 13, that is:

a) a prokaryote cell;

b) *E. coli;* c) an eukaryote cell; or d) a COS cell.

20. A method of producing antigenic IL-10-like polypeptide comprising culturing a host cell of claim 13 thereby producing said IL-10-like polypeptide; and recovering said polypeptide.

21. The method of claim 20, wherein said vector comprises the mature polypeptide encoding portion of SEQ ID NO: 1.

22. The method of claim 21, wherein said host cell is eukaryotic.

23. The polynucleotide of claim 9, wherein T is U.

24. A recombinant expression vector encoding amino acid residues 1 to 150 of SEQ ID NO: 2.

25. A cell comprising said vector of claim 24.

26. The vector of claim 25, comprising nucleotides 99 to 548 of SEQ ID NO: 1.

27. A method of producing a polypeptide, comprising culturing a cell of claim 26 thereby producing an IL-10-like polypeptide, and recovering said polypeptide.

28. An isolated or recombinant polynucleotide that is the complement of said polynucleotide of claim 2.

29. A method of producing an antigenic IL-10-like polypeptide, comprising culturing a host cell comprising an expression vector comprising the sequence complementary to said polynucleotide of claim 9 thereby producing said IL-10-like polypeptide; and recovering said polypeptide.

* * * * *